United States Patent [19]

Cortese et al.

[11] Patent Number: 4,731,122

[45] Date of Patent: Mar. 15, 1988

[54] PROCESS FOR MANUFACTURING A THERMOPLASTIC MOLDING COMPOSITION

[75] Inventors: Richard Cortese, Los Gatos; Jeremy C. Wright; James B. Eckenhoff, both of Los Altos; David L. Rivera, San Jose, all of Calif.

[73] Assignee: ALZA Corporation, Pala Alto, Calif.

[21] Appl. No.: 31,824

[22] Filed: Mar. 30, 1987

[51] Int. Cl.[4] ............................................. C08L 1/08
[52] U.S. Cl. ................................. 106/198; 106/181; 424/473
[58] Field of Search ............... 106/198, 181, 196, 169; 424/473, 424; 514/311; 604/892

[56] References Cited

U.S. PATENT DOCUMENTS

| | | | |
|---|---|---|---|
| 3,015,570 | 1/1962 | Bowman et al. | 106/181 |
| 4,077,407 | 3/1978 | Theeuwes et al. | 106/196 |
| 4,235,236 | 11/1980 | Theeuwes | 604/892 |
| 4,320,759 | 3/1982 | Theeuwes | 604/892 |

*Primary Examiner*—Paul Lieberman
*Assistant Examiner*—Helene Kirschner
*Attorney, Agent, or Firm*—Paul L. Sabatine; Edward L. Mandell; Shelley G. Precivale

[57] ABSTRACT

The invention concerns a process for producing a thermoplastic composition comprising a cellulose ester.

3 Claims, No Drawings

PROCESS FOR MANUFACTURING A THERMOPLASTIC MOLDING COMPOSITION

FIELD OF THE INVENTION

This invention pertains to a process for manufacturing a thermoplastic molding composition. The molding composition is useful for fabricating a wall having improved properties of a beneficial agent delivery device.

DESCRIPTION OF THE INVENTION

This invention concerns a process for providing a termoplastic moldable composition. The composition comprises generally, in one embodiment, at least one of from 0 to 100% of a cellulose acetate butyrate, from 100 to 0 cellulose acetate, at least one of from 0 to 30% tributyl citrate, from 0 to 30% triethyl citrate and from 0 to 10% of polyethylene glycol, with the amount of all the thermoplastic, molding-forming ingredients equal to 100%. In a more specific preferred embodiment, the composition comprises from 35% to 70% of cellulose acetate butyrate, from 10% to 40% cellulose aetate, from 15% to 30% tributyl citrate, from 5% to 30% triethyl citrate, and from 1% to 10% of polyethylene glycol, with the amount of all the thermoplastic, molding-forming ingredients equal to 100%. The thermoplastic composition, in another presently preferred embodiment, comprises 57% cellulose acetate butyrate having 17% butyryl groups, 29.5% acetyl groups and 1 hydroxyl group for each four anhydroglucose group, 13% cellulose acetate having a 39.8% acetyl content, 20% tributyl citrate, 7% triethyl citrate and 3% polyethylene glycol having a molecular weight of about 400; in another preferred embodiment the thermoplastic composition comprises 49% cellulose acetate butyrate comprising 17% butyryl groups, 29.5% acetyl groups and 1 hydroxyl group for four each anhydroglucose unit, 17% cellulose acetate comprising 39.8% acetyl content, 22% tributyl citrate, 8% triethyl citrate, and 4% polyethylene glycol having a molecular weight of about 400. The thermoplastic molding-forming compositions generally exhibit a bulk density of $\geq 0.5$ grams/cm$^3$, a nominal granule size of 0.635 cm, and a flow characteristic of 400 gram per minute through a 3.5 cm diameter orifice. The thermoplastic compositions can be used in comparison molding, transfer molding, injection molding, blow molding, and rotational molding techniques for producing the wall structure of a beneficial agent delivery device.

The process of the invention, in one presently preferred process, for producing the thermoplastic composition, comprises the steps of (a) comminuting bulk cellulose acetate butyrate with a comminutor such as a Fitzpatrick Model D to particle size that pass through a number 10 screen; (b) blending in a separate mixing vessel tributyl citrate, triethyl citrate and polyethylene glycol for 15 to 30 minutes mixing time for producing a uniform blend; (c) adding cellulose acetate butyrate to the uniform blend and mix for a few minutes; (d) add cellulose acetate to the cellulose acetate butyrate blend and mix all the ingredients for 15 to 30 minutes to produce the thermoplastic composition; (e) compacting the thermoplastic composition in a roller compaction machine to produce a ribbon comprising the compacted composition; and, (f) grinding the compacted composition into pellets sized for feeding to a molding machine.

The process of the invention, in another preferred process, provides a thermoplastic composition, with the components expressed in percent by weight as follows: 49% cellulose acetate butyrate, 17% cellulose acetate, 22% tributyl citrate, 8% triethyl citrate and 4% polyethylene glycol. The composition was prepared as follows: first, mixing in a blender, by adding in turn, 120 g of triethyl citrate, 330 g of tributyl citrate, and 60 g of polyethylene glycol and mixing the three ingredients at a low rate of mixing for a few minutes; then, adding to the blender with continuous mixing 735 g of cellulose acetate butyrate and continuing the mixing for a few minutes; then, adding with continuous mixing 255 g of cellulose acetate and continue blending for 15 to 30 minutes to yield the thermoplastic composition. Next, the thermoplastic composition is compacted by passing the composition through a roller compactor operation under a pressure of 500 psig a roll speed of 18 RPM, with the roll temperature cooled by standard running water. The compacted composition was passed through a granulator, and the granules stored in polyethylene lined drums.

A number of walled containers formed with a thermoplastic composition and having an opening at one end were prepared in an injection molding machine operated under the following conditions: rear zone temperature 300° F.; front zone temperature 328° F.; nozzle zone temperature 330° F.; hot tip temperature 475° F.; injection boost pressure 1500–1800 psig; injection hold pressure 1000 psig; mold open time 4 seconds; mold closed time 5.5 seconds; core pin temperature 55° F.; stationary platen temperature 80° % F.; stripper plate temperature 40° F.; and mode fully atomatic.

The process provides a thermoplastic composition that can be used for the economical making of drug delivery systems for administering a drug to an animal. The compositions are nontoxic and devices made using the thermoplastic composition can be used for prolonged periods in the gastrointestinal tract and subcutaneous tissue of humans or animals.

While there has been described and pointed out features of the invention as applied to presently preferred embodiments, those skilled in the art will appreciate that various modifications, changes, additions and omissions in the system illustrated and described can be made without departing from the spirit of the invention.

We claim:

1. A process for the manufacture of a thermoplastic composition, wherein the composition comprises: at least one member selected from the group consisting of cellulose acetate butyrate and cellulose acetate, at least one of a member selected from the group consisting of tributyl citrate and triethyl citrate and wherein the process sequentially comprises: comminuting cellulose acetate butyrate to a smaller particle size; blending at least one member of tributyl citrate, and triethyl citrate, and polyethylene glycol to a uniform blend; adding the comminuted cellulose acetate butyrate to the continuously mixing blend; adding the cellulose acetate to the blending ingredient and blend to produce a homogeneous thermoplastic composition; compacting the thermoplastic composition to produce a compacted composition; and, granulating the compacted composition into granules sized for use in a molding machine.

2. The process for manufacturing the thermoplastic composition according to claim 1, wherein the composition comprises polyethylene glycol.

3. A process for producing a thermoplastic molding composition, wherein the process comprises the steps of: mixing tributyl citrate, triethyl citrate and polyethylene glycol to yield a first mixture; adding to the mixing first mixture cellulose acetate butyrate to produce a second mixture; adding to the mixing second mixture cellulose acetate to produce a thermoplastic composition comprising cellulose acetate butyrate, cellulose acetate, tributyl citrate, triethyl citrate and polyethylene glycol; compacting the thermoplastic composition into a compacted mass; and grinding the compacted composition into particles sized for admittance into a molding machine.

* * * * *